US011648390B2

(12) United States Patent
Spanier et al.

(10) Patent No.: US 11,648,390 B2
(45) Date of Patent: *May 16, 2023

(54) INTRAVASCULAR BLOOD PUMP

(71) Applicant: ABIOMED EUROPE GMBH, Aachen (DE)

(72) Inventors: Gerd Spanier, Aachen (DE); Frank Kirchhoff, Aachen (DE); Thorsten Siess, Wuerselen (DE); Dirk Michels, Aachen (DE)

(73) Assignee: ABIOMED EUROPE GMBH, Aachen (DE)

(*) Notice: Subject to any disclaimer, the term of this patent is extended or adjusted under 35 U.S.C. 154(b) by 142 days.

This patent is subject to a terminal disclaimer.

(21) Appl. No.: 16/802,660

(22) Filed: Feb. 27, 2020

(65) Prior Publication Data

US 2020/0261633 A1   Aug. 20, 2020

Related U.S. Application Data

(63) Continuation of application No. 15/375,477, filed on Dec. 12, 2016, now Pat. No. 10,610,626, which is a (Continued)

(30) Foreign Application Priority Data

Feb. 16, 2012   (DE) .......................... 102012202411.5

(51) Int. Cl.
*A61M 60/00* (2021.01)
*A61M 60/824* (2021.01)
(Continued)

(52) U.S. Cl.
CPC ........ *A61M 60/824* (2021.01); *A61M 60/122* (2021.01); *A61M 60/13* (2021.01);
(Continued)

(58) Field of Classification Search
CPC .............. A61M 60/829; A61M 60/122; A61M 60/824; A61M 60/422; A61M 60/205
See application file for complete search history.

(56) References Cited

U.S. PATENT DOCUMENTS

| 4,704,121 A | 11/1987 | Moise |
| 4,944,722 A * | 7/1990 | Carriker .............. F04D 29/0413 600/16 |

(Continued)

FOREIGN PATENT DOCUMENTS

| DE | 202009018145 U1 | 5/2011 |
| EP | 0904117 A1 | 3/1999 |

(Continued)

OTHER PUBLICATIONS

International Search Report dated Apr. 24, 2013 for International Application No. PCT/EP2013/053001, International Filing Date Feb. 14, 2013.

(Continued)

*Primary Examiner* — Eric D. Bertram
(74) *Attorney, Agent, or Firm* — Botos Churchill IP Law LLP

(57) ABSTRACT

An intravascular blood pump having a drive section (11), a catheter (14) fastened to the drive section proximally and a pump section (12) fastened to the drive section distally possesses an electric motor (21) whose motor shaft (25) is mounted in the drive section (11) with two radial sliding bearings (27, 31) and an axial sliding bearing (40). During operation, purge fluid is conveyed through the bearing gap of the axial sliding bearing (40) and further through the radial sliding bearing (31) at the distal end of the drive section (11). The purge fluid is highly viscous, for example 20% glucose solution.

19 Claims, 6 Drawing Sheets

Figure 1:
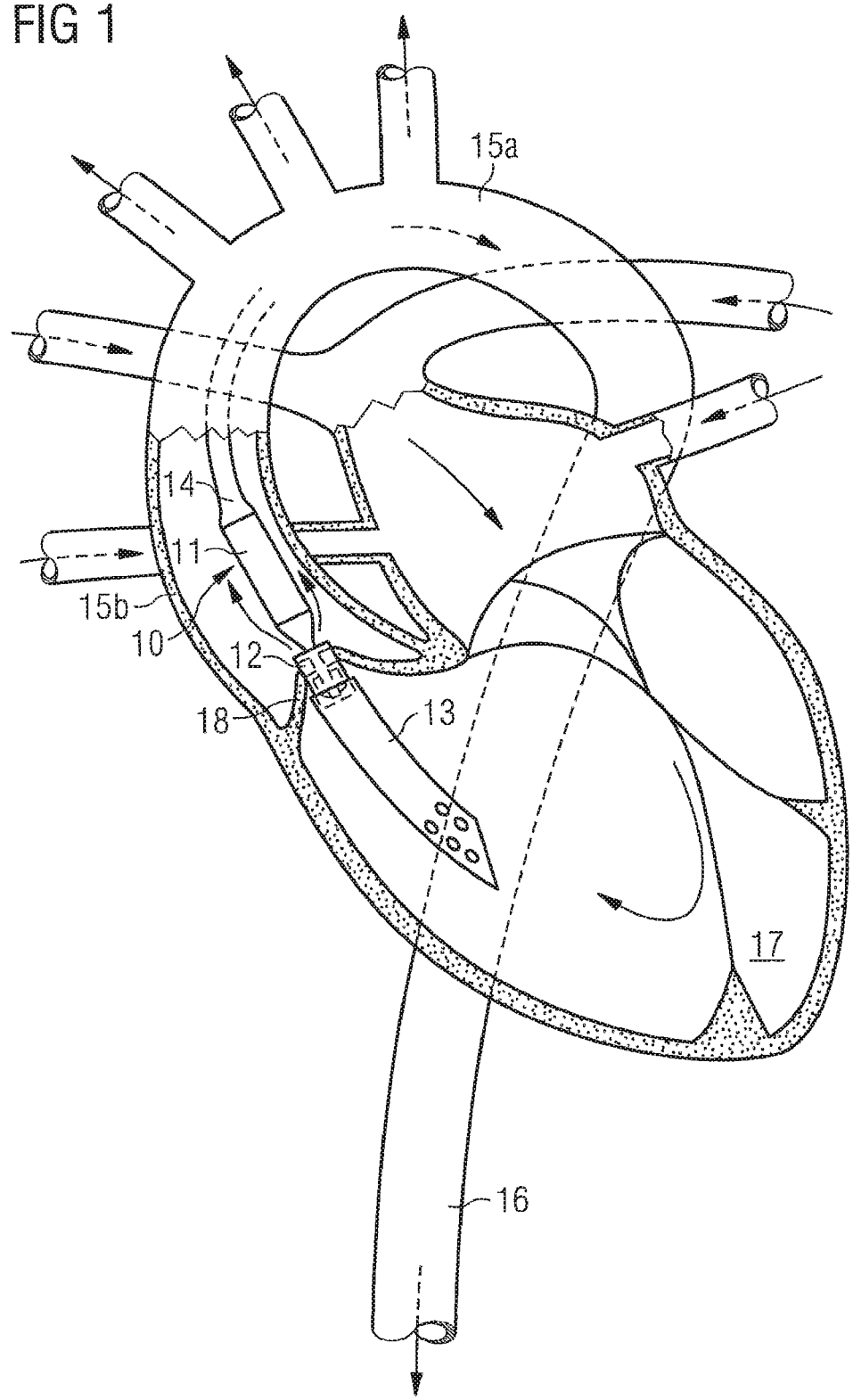

Related U.S. Application Data continuation of application No. 14/377,704, filed as application No. PCT/EP2013/053001 on Feb. 14, 2013, now Pat. No. 9,550,017.

(51) Int. Cl.
| | |
|---|---|
| *A61M 60/422* | (2021.01) |
| *A61M 60/829* | (2021.01) |
| *A61M 60/122* | (2021.01) |
| *A61M 60/237* | (2021.01) |
| *A61M 60/13* | (2021.01) |
| *A61M 60/148* | (2021.01) |
| *A61M 60/165* | (2021.01) |

(52) U.S. Cl.
CPC ........ *A61M 60/237* (2021.01); *A61M 60/422* (2021.01); *A61M 60/829* (2021.01); *A61M 60/148* (2021.01); *A61M 60/165* (2021.01)

(56) References Cited

U.S. PATENT DOCUMENTS

| | | | |
|---|---|---|---|
| 5,211,546 A | 5/1993 | Isaacson et al. | |
| 5,911,685 A * | 6/1999 | Siess | H02K 5/132 |
| | | | 600/16 |
| 5,964,694 A | 10/1999 | Siess et al. | |
| 6,158,984 A * | 12/2000 | Cao | A61M 60/422 |
| | | | 417/423.1 |
| 6,176,848 B1 * | 1/2001 | Rau | F04D 29/047 |
| | | | 600/16 |
| 7,011,620 B1 | 3/2006 | Siess | |
| 9,550,017 B2 * | 1/2017 | Spanier | A61M 60/122 |
| 10,610,626 B2 * | 4/2020 | Spanier | A61M 60/122 |
| 2007/0015600 A1 | 1/2007 | Breier et al. | |
| 2007/0156006 A1 | 7/2007 | Smith et al. | |
| 2008/0269880 A1 * | 10/2008 | Jarvik | F04D 13/0633 |
| | | | 384/129 |
| 2010/0017413 A1 | 1/2010 | James | |
| 2010/0174131 A1 * | 7/2010 | Foster | A61M 60/422 |
| | | | 600/16 |
| 2011/0282128 A1 | 11/2011 | Reitan et al. | |
| 2011/0282212 A1 | 11/2011 | Hyoun et al. | |

FOREIGN PATENT DOCUMENTS

| | | |
|---|---|---|
| EP | 0961621 A1 | 12/1999 |
| JP | 2000512191 A | 9/2000 |
| JP | 2002315824 A | 10/2002 |
| WO | 8501436 A1 | 4/1985 |
| WO | 9843688 A1 | 10/1998 |
| WO | 2009046790 A2 | 4/2009 |
| WO | 2009157840 A1 | 12/2009 |

OTHER PUBLICATIONS

Office Action from corresponding Korean Application No. 10-2022-7011887 dated Aug. 11, 2022 (12 pages).

* cited by examiner

INTRAVASCULAR BLOOD PUMP

CROSS-REFERENCE TO RELATED APPLICATIONS

This application is a continuation of U.S. patent application Ser. No. 15/375,477, filed Dec. 12, 2016 (now U.S. Pat. No. 10,610,626) which is a continuation of U.S. patent application Ser. No. 14/377,704, filed on Aug. 8, 2014 (now U.S. Pat. No. 9,550,017), which is a U.S. National Stage Application Under 35 U.S.C. § 371 of International Patent Application No. PCT/EP2013/053001, filed on Feb. 14, 2013 (now expired), which claims priority to German Patent Application No. 102012202411.5, filed Feb. 16, 2012. The specifications of each of the foregoing applications are incorporated herein by reference in their entirety.

This invention relates to an intravascular blood pump for supporting blood circulation in human or optionally also animal bodies. It is inserted percutaneously for example into the femoral artery and guided through the body's vascular system in order, for example, to support or replace the pumping action in the heart. The invention likewise relates to a system comprising such an intravascular blood pump, and to a method for supporting blood circulation while employing such an intravascular blood pump.

The requirements to be met by such blood pumps with regard to duration of service and small size are continually increasing. The smallest pumps of this kind have an outer diameter of about 4 mm. A further reduction of the outer diameter is limited, inter alia, by the machine elements employed within the pump, which are not available in arbitrarily small sizes. Furthermore, the machine elements are subjected to enormous loads, since these pumps work at high rotational speeds of several 10,000 turns per minute on account of the small package size and the substantial volume flows to be conveyed in human blood circulation. While blood pumps of this kind were originally intended only for short-term heart support, they are increasingly also being used for long-term treatment over several days up to weeks.

From EP 0 961 621 B1 there is known an intravascular blood pump that possesses a drive section, a catheter attached at the proximal end of the drive section and having lines extending therethrough for the power supply to the drive section, and a pump section fastened at the distal end of the drive section. The drive section comprises a motor housing having an electric motor disposed therein, with the motor shaft of the electric motor distally protruding out of the drive section and into the pump section. The pump section in turn comprises a tubular pump housing having an impeller rotating therein which is seated on the end of the motor shaft protruding out of the motor housing. The motor shaft is mounted in the motor housing in exactly two bearings which are maximally removed from each other in order to guarantee a true, exactly centered guidance of the impeller within the pump housing. While a radial ball bearing is used in practice for the bearing at the proximal end of the motor housing, the impeller-side bearing is moreover configured as a shaft seal, in order to prevent blood from entering the motor housing. In practice, the entry of blood into the motor housing is furthermore counteracted by a purge fluid being passed through the motor housing and the impeller-side bearing configured as a shaft seal. This is done at a purge-fluid pressure that is higher than the blood pressure present.

The intravascular blood pump normally conveys the blood through the pump housing and past the motor housing from distal to proximal. A reverse conveying direction is also possible. In both cases the impeller, when conveying the blood, produces axial forces that are transferred to the bearings via the motor shaft and taken up by the radial ball bearing.

Starting out from this prior art, it is the object of the present invention to propose measures for how to further reduce the package size of such intravascular blood pumps and increase their service life.

This object is achieved by an intravascular blood pump having the features of claim 1. Claims dependent thereon state advantageous developments and embodiments of the invention.

The blood pump according to the invention is characterized in that it is mounted in the motor housing axially by means of an axial bearing, the axial bearing being an axial sliding bearing or combined radial-axial sliding bearing. The axial forces of the motor shaft thus no longer need to be taken up by the radial ball bearing disposed at the proximal end of the motor housing. The radial ball bearing can hence be constructed accordingly smaller or be replaced by another compact radial bearing, in particular a radial sliding bearing. This in turn makes it possible to develop blood pumps having a further reduced outer diameter.

At the same time, this measure prolongs the service life of the blood pump, because the radial bearing is relieved on account of the reduced axial forces, which a radial bearing is not primarily intended to take up anyway, so that it is subject to less wear.

Alternatively, the invention can be integrated into existing package sizes in order to increase service life and reduce the degree of complexity.

The axial forces acting on the motor shaft are contrary to the conveying direction. When the blood pump is arranged for conveying alternatively in the proximal direction and in the distal direction, axial forces act on the motor shaft in the distal direction in one case and in the proximal direction in the other case. In such a blood pump, two axial sliding bearings or axial-radial sliding bearings are accordingly to be provided in the motor housing for axially mounting the motor shaft. The axial sliding bearing can be formed in a simple manner by a disk disposed on the motor shaft and supported against a circumferential shoulder of the motor housing. In the case of an axial-radial sliding bearing, the disk possesses a convex or concave, in particular spherical, bearing surface. Hereinafter the term "axial sliding bearing" will be employed synonymously for both variants, the axial sliding bearing and the radial-axial sliding bearing.

The motor housing itself is filled with a suitable fluid which forms a lubricating film in the bearing gap of the axial sliding bearing. Alternatively, purge fluid fed through a purge-fluid feed line and flowing through the radial bearing located at the distal end of the motor housing can also flow through the bearing gap of the axial sliding bearing and in this manner be used for forming the lubricating film in the bearing gap. To ensure in this case that the purge fluid reaches the distal radial bearing at a pressure higher than the blood pressure present, there can be provided, in at least one of the surfaces forming the bearing gap of the axial sliding bearing, a channel which penetrates the bearing gap from radially outward to radially inward, so that the purge fluid can flow through this channel to the distal radial bearing. This channel need not necessarily lie in a bearing-gap surface, but can also be realized as a separate channel or as a bore. However, providing the channel in one of the hearing-gap surfaces has the advantage that the lubricating film in the bearing gap heats up less, because a part of the lubricating film is continually being replaced by purge fluid flowing in later. Preferably, the channel is located in the stationary bearing-gap surface in order to minimize the radial conveying capacity.

Preferably, the axial sliding bearing is configured as a hydrodynamic sliding bearing. In contrast to a simple sliding bearing, in a hydrodynamic sliding bearing a pressure is built up in the lubricating film through the pumping action of the two surfaces moved relative to each other. For this purpose, according to a preferred variant, the bearing gap can be configured as a converging gap in some regions in the circumferential direction of the axial sliding bearing. In this connection the moved surface is preferably even, that is, the opposing stationary surface of the bearing gap has ramps which converge toward the moved surface in the rotation direction of the moved surface. Thus there is formed in the bearing gap a wedge into which the lubricating fluid is transported, thereby building up a pressure causing the moved surface to move away from the static surface. In this state, sliding friction prevails on a fluid film, said friction being virtually wear-free. Since the blood pump normally conveys continuously at high rotational speed, the blood pump has especially low wear and is accordingly suitable for long-term applications.

In the simplest embodiment, the moved disk can be configured as a wobble disk and form the convergent gap or wedge simply through the slant.

Instead of the bearing gap having converging surface zones, one of the surfaces forming the bearing gap can have one or more spirally disposed grooves. In this case, the lubricating fluid is pumped along the grooves toward the center of the bearing through the relative motion of the two surfaces, and builds up a pressure there which in turn leads to the two surfaces moving away from each other. In the spiral-groove bearing variant, it is preferred to provide the spirally disposed grooves in the moved surface, because this makes the conveying of lubricating fluid into the grooves more effective.

Should the axial thrust ($F_{axMotor}$) of the pumping apparatus be greater than the load-carrying capacity of the axial sliding bearing for design reasons, the axial thrust of the pumping apparatus can be compensated partly through a suitable axial arrangement of the rotating magnet in the motor. According to the invention, the rotating magnet behaves like a solenoid which strives magnetically to be situated in the center of the static motor section. When it is now pulled out of this rest position, a magnetic force arises in the reverse direction ($F_{axMagnet}$). This force can be used in the direction of the axial thrust ($F_{axMotor}$) for further axial stabilization or in the opposite direction and relieve the axial sliding bearing. Further, the resultant force on the axial bearing can be adjusted by varying the pressure of the purge fluid (cf. FIG. 2).

It is further preferred when the surfaces forming the bearing gap of the axial sliding bearing are made of ceramic, preferably zirconium oxide. Surfaces made of ceramic have high strength and low wear. In particular, the total distal end of the motor housing, including the surface for the axial sliding bearing, can be manufactured from a one-piece ceramic part in a simple manner, so that the total manufacturing costs of the blood pump are low.

The lead wires of the electric motor received in the motor housing are normally guided around the proximally situated radial bearing on the outside and electroconductively connected, in particular soldered, to the power supply lines extending within the catheter. According to a preferred embodiment of the invention, the lead wires of the electric motor are now guided through the outer ring of the radial bearing or advantageously within one or more radially outer slots of the outer ring. This saves overall space in the radial direction, which is in turn positive for the development of blood pumps having a small outer diameter. It is thus for example possible to obtain space for a pressure measurement and its implementation at the proximal motor end.

The lead wires can advantageously be soldered to the power supply lines on a surface of the motor housing proximally of the proximally situated radial bearing. This is advantageous because electrically connecting the lead wires of the electric motor to the power supply tines directly can cause difficulties on account of the small thickness of the lead wires and the relatively great thickness of the power supply lines. When the relevant surface of the electric motor is made of a plastic or of ceramic, as to be explained hereinafter, the soldering-point region can be coated conductively, for example with copper, before soldering, and the soldering of the lead wires and of the supply lines is respectively effected separately in this region.

Preferably, the relevant part of the motor housing is subsequently embedded into plastic, with the soldering points and preferably also the motor windings being embedded as well, so that the soldering points are electrically isolated, on the one hand, and mechanically protected, on the other hand.

According to a preferred development of the invention, the radial bearings for the motor shaft are also respectively configured as sliding bearings at the proximal end and at the distal end of the motor housing. Since these radial bearings serve substantially only for guiding the shaft in an exactly centered manner and accordingly only low radial forces are to be taken up, they can be configured as simple sliding bearings. A radial sliding bearing requires considerably less overall space in the radial direction than a rolling-element bearing with its inner and outer rings. This again has a positive effect on the possibilities of manufacturing blood pumps having a small outer diameter.

In particular, it is preferred to make the radial sliding bearing located at the proximal end of the motor housing of ceramic, with the ceramic bearing lying directly against the circumferential surface of the motor shaft. The radial bearing located at the distal end of the motor housing can also be configured in a corresponding manner. The surface of the motor shaft opposing the ceramic surface, which together with the ceramic surface forms the bearing gap of the radial sliding bearing, is preferably coated with an amorphous carbon coating (DLC=diamond-like carbon or diamond-like coating). DLC layers are especially wear-resistant and low-friction. They are only a few micrometers thick and can be produced for example by chemical vapor deposition (CVD) or physical vapor deposition (PVD). Alternatively, the shaft can be made of a breakproof ceramic.

During operation, the blood pump is attached to a purge-fluid source, and fluid passed into the motor housing through the purge-fluid line. The purge fluid then flows through the axial sliding bearing and further through the distal radial bearing. In the axial sliding bearing it forms the lubricating film in the bearing gap. The pressure at which the purge fluid flows through the motor housing has an adverse effect, however, on the width of the bearing gap. For the higher the purge-fluid pressure is, the smaller the bearing-gap width becomes and the thinner the lubricating film between the sliding surfaces is. The thinner the lubrication film is, the greater in turn the motor current for driving the electric motor is that is necessary for overcoming the frictional forces. This is unfavorable for the control of the blood pump, because the current conveying volume is normally established by stored characteristic curves solely on the basis of the motor current and the rotational speed (both known quantities). When the purge-fluid pressure additionally affects the motor current, a further influence quantity would have to be taken into consideration. In view of the fact that the same blood-pump type can be operated for a great variety of applications with different purge-fluid pressures between 300 and 1400 mmHg, it is important to avoid a dependence of motor current on purge-fluid pressure.

This can actually be obtained when there is chosen as a purge fluid a fluid having a viscosity that is considerably higher than the viscosity of water ($\eta$=0.75 mPa·s at 37° C.). For with a highly viscous purge fluid, the fluid film is maintained even at high pressures and the friction of the axial sliding bearing is accordingly independent of the purge-fluid pressure. It has turned out that the axial sliding bearing can be configured as a simple sliding bearing, and does not have to be configured as a hydrodynamic sliding bearing, with a purge fluid whose viscosity at 37° C. amounts to approx. 1.2 mPa·s or higher. Good results were achieved for example with a ≥20% glucose solution between ceramic surfaces made of zirconium oxide.

Figure 2:
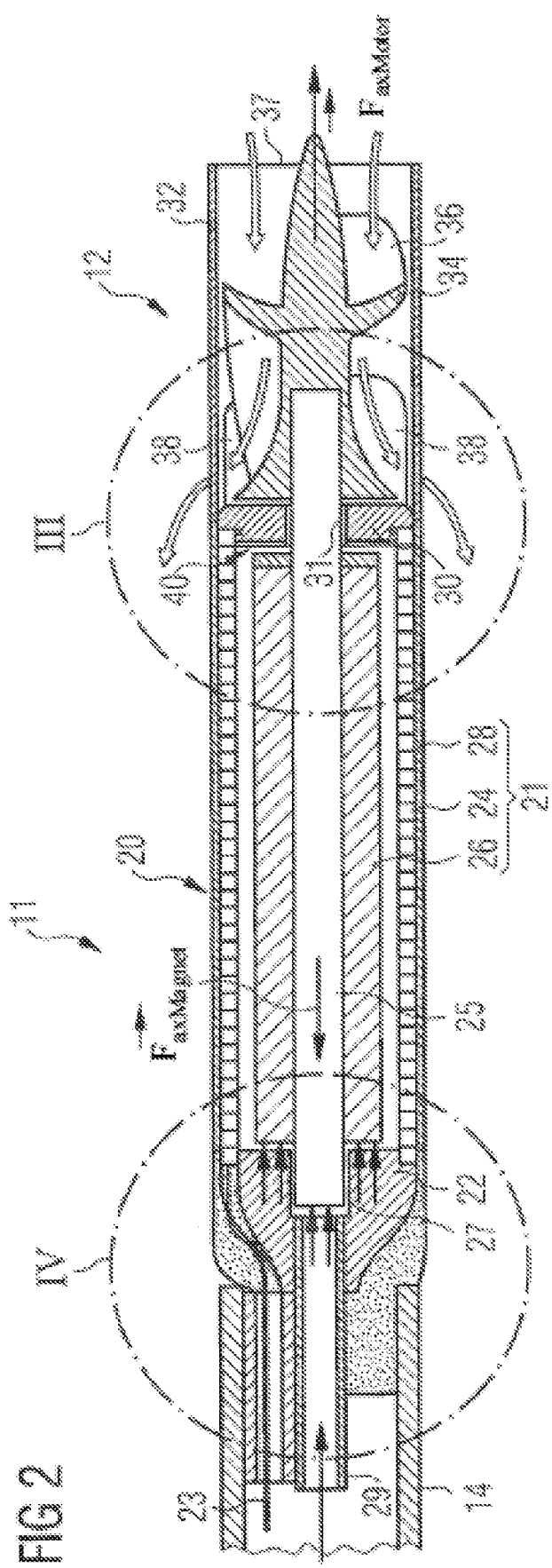
Figure 3:
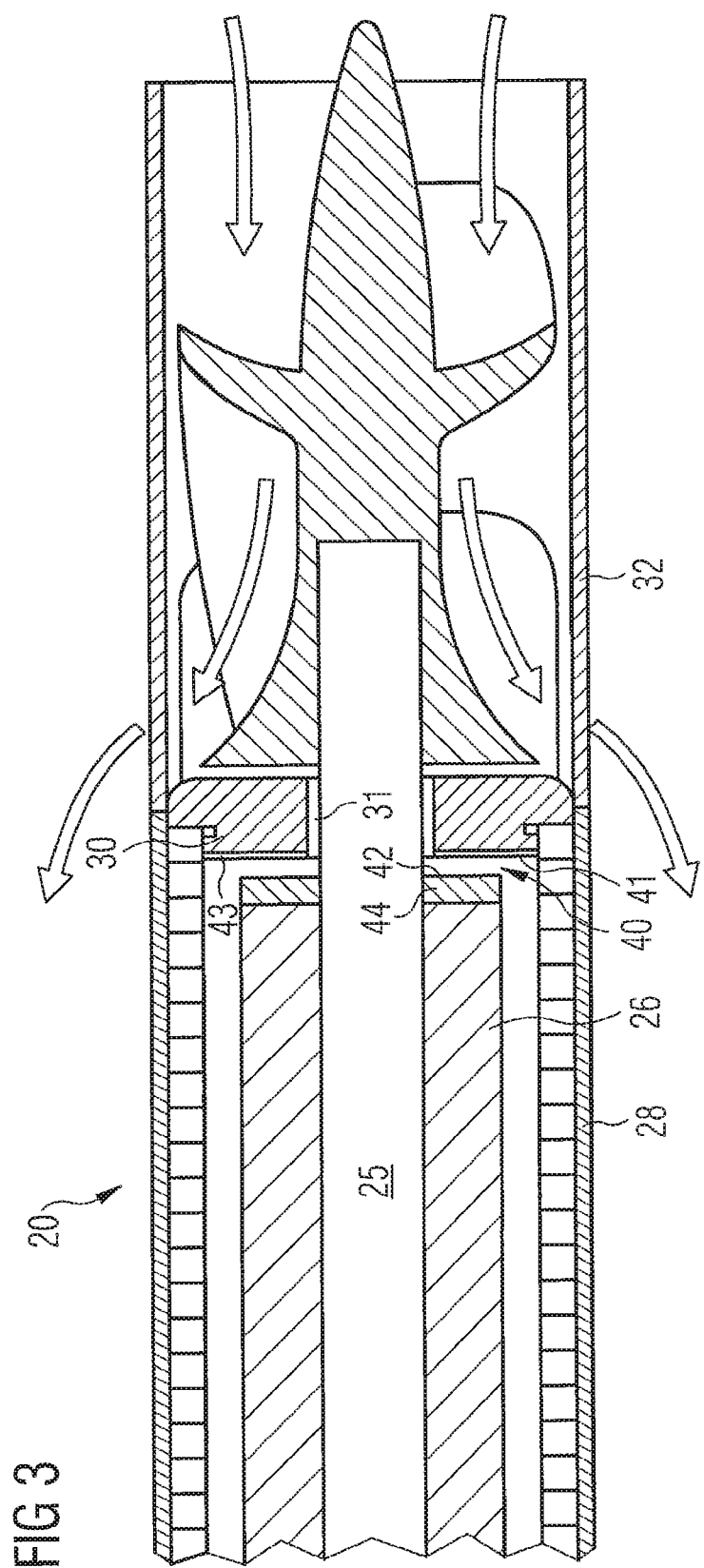
Figure 4:
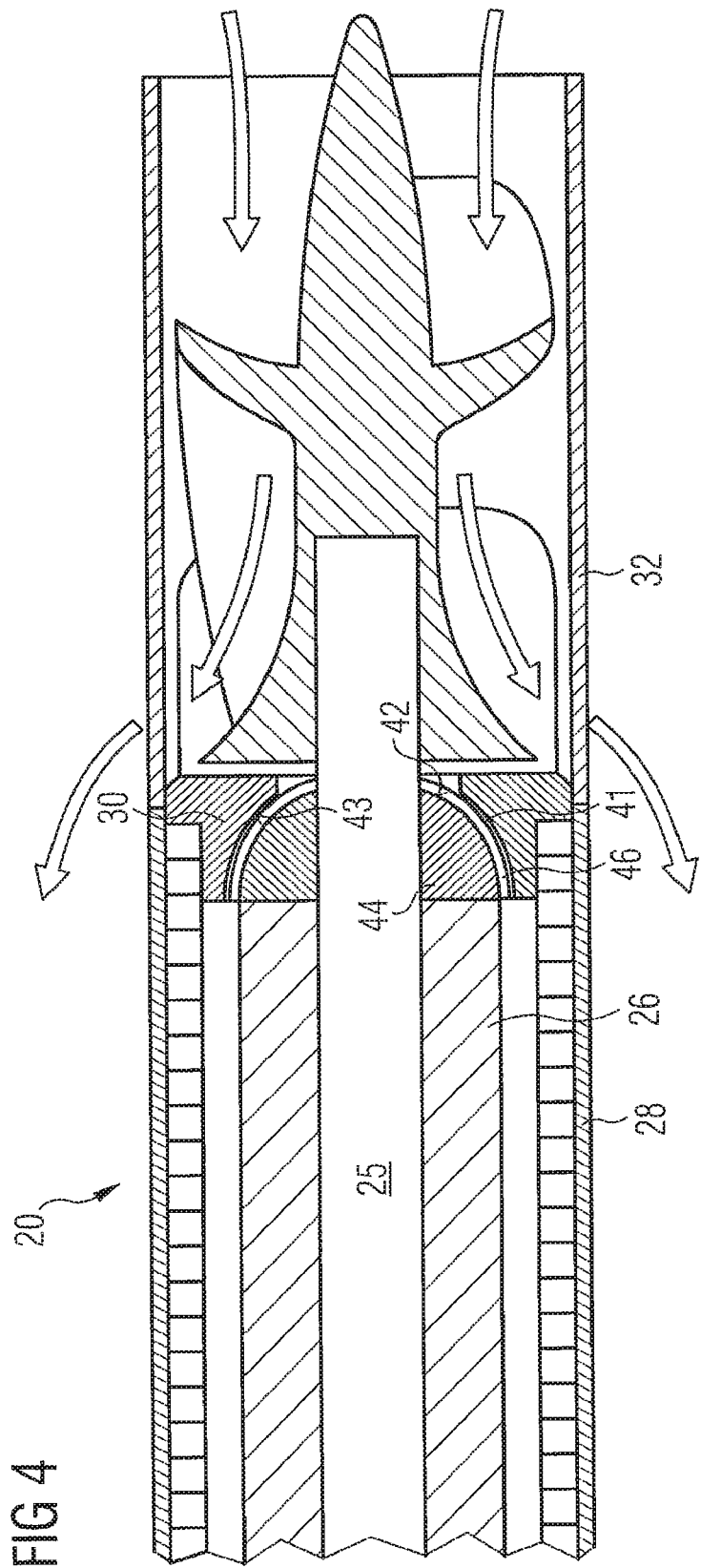
Figure 5:
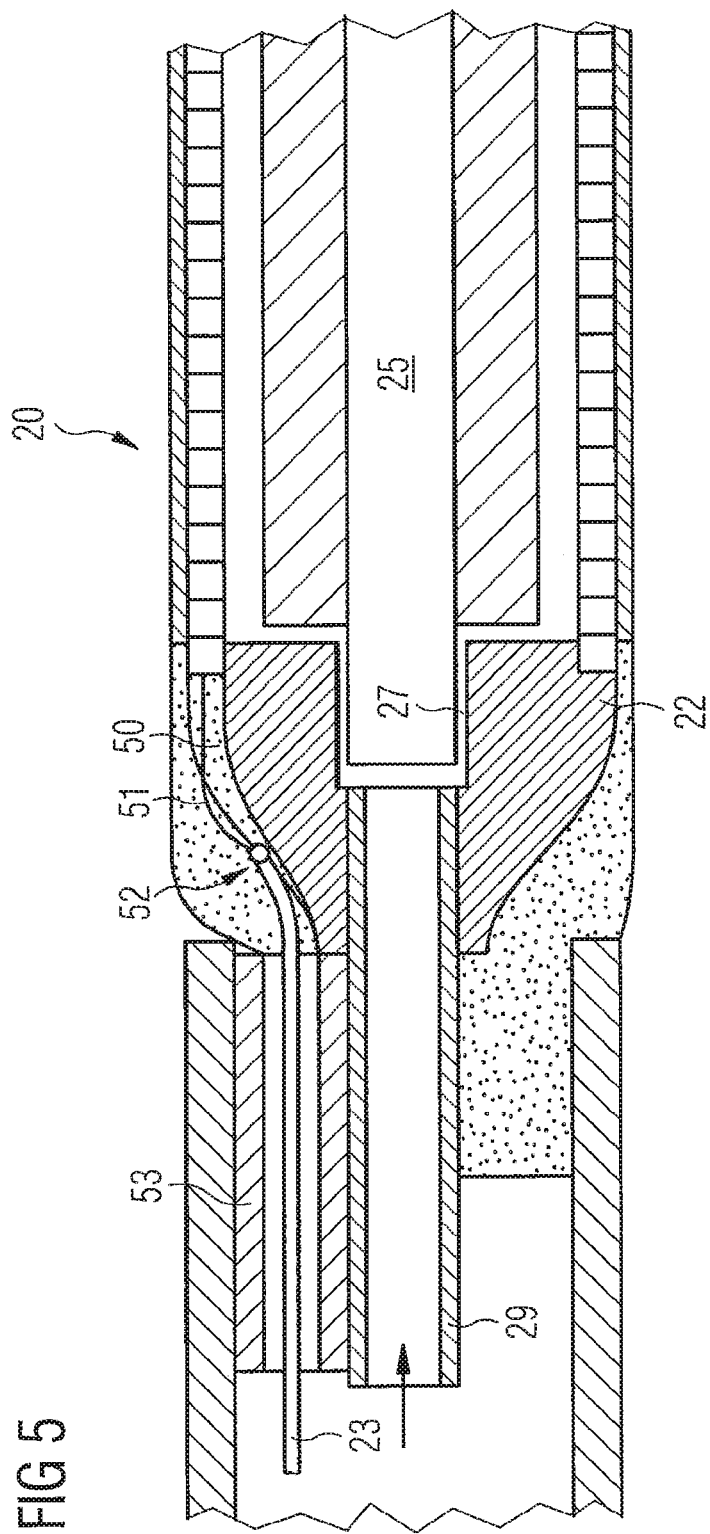
Figure 6A:
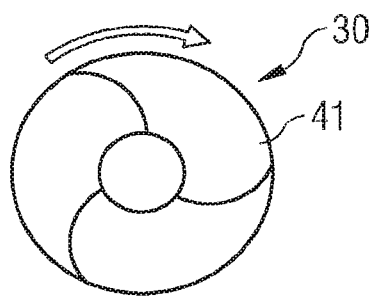
Figure 6B:
Figure 7:
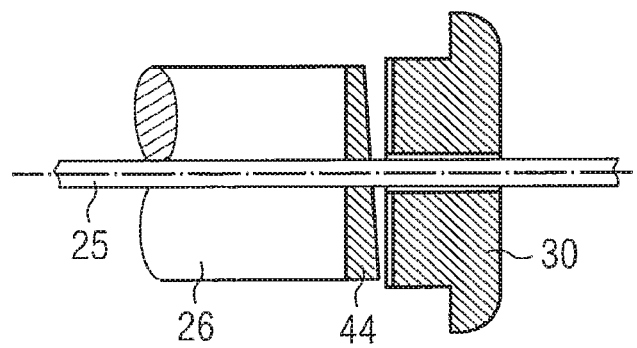
Figure 8:
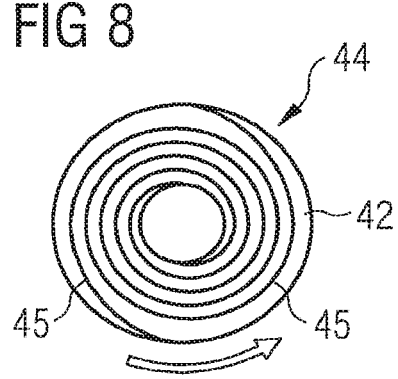

Hereinafter the invention will be explained by way of example with reference to the accompanying drawings. Therein are shown:

FIG. 1 a schematic representation of the insertion of a blood pump before the left ventricle, with positioning of its inflow cannula within the left ventricle, FIG. 2 a schematic longitudinal section of an exemplary embodiment of the blood pump, FIG. 3 an enlarged representation of the detail III from FIG. 2, FIG. 4 a variant of the detail III from FIG. 3, FIG. 5 an enlarged representation of the detail IV from FIG. 2, FIGS. 6A and 6B an axial sliding bearing surface in plan view and as a development according to a first exemplary embodiment, FIG. 7 an axial sliding bearing surface in cross section according to a second exemplary embodiment, and FIG. 8 an axial sliding bearing surface in plan view according to a third exemplary embodiment.

FIG. 1 represents the employment of a blood pump 10 for supporting the left ventricle. The blood pump has a motor section 11 and a pump section 12 which are disposed coaxially one behind the other and result in a rod-shaped construction form. The pump section is extended by a flexible suction hose 13 which has, at its end and/or in its side wall, openings for the entry of blood to the pump. The end of the blood pump 10 facing away from the suction hose 13 is connected to a catheter 14, which has been inserted through the aortic arch 15a and the aorta 16. The blood pump 10 is so placed that it lies primarily in the ascending aorta 15b, whereas the pump section 12 with the suction hose 13 lies substantially in the left ventricle 17. The aortic valve 18 comes to lie, in the closed state, against the outer side of the pump housing or of the suction hose 13. The blood pump 10 with the suction hose 13 in front is advanced into the represented position by advancing the catheter 14, optionally employing a guide wire. In so doing, the suction hose 13 passes the aortic valve 18 retrograde, so that blood is sucked in through the suction hose 13 and pumped into the aorta 16. Thus far, the blood pump corresponds to the blood pump known from EP 0 961 621 B1.

The use of the blood pump is not restricted to the application represented in FIG. 1, which merely involves a typical example of application. Thus, the pump can also be inserted through other peripheral vessels, such as the subclavian artery, or also be placed in the right heart.

FIG. 2 shows a preferred exemplary embodiment of the blood pump with the motor section 11 and the pump section 12 firmly connected thereto. The motor section 11 has an elongate housing 20 in which the electric motor 21 is housed. The stator 24 of the electric motor 21 has, in the usual way, numerous circumferentially distributed windings as well as a magnetic return path 28 in the longitudinal direction. It is firmly connected to the motor housing. The stator 24 surrounds the rotor 26 connected to the motor shaft 25 and consisting of permanent magnets magnetized in the active direction. The motor shaft 25 extends over the total length of the motor housing 20 and protrudes distally out of the latter. There, it carries an impeller 34 with vanes 36 projecting therefrom or pump vanes which rotate within a tubular pump housing 32 which is in turn firmly connected to the motor housing 20.

The proximal end of the motor housing 20 has the flexible catheter 14 sealingly attached thereto. Through the catheter 14 there extend electrical cables 23 for power supply to and control of the electric motor 21. There additionally extends through the catheter 14 a purge-fluid line 29 which penetrates the proximal end wall 22 of the motor housing 20. Purge fluid is fed through the purge-fluid line 29 into the interior of the motor housing 20 and exits through the end face 30 at the distal end of the motor housing. The purging pressure is so chosen that it is higher than the blood pressure present, in order to thereby prevent blood from penetrating into the motor housing, being between 300 and 1400 mmHg depending on the case of application.

Upon a rotation of the impeller 34, blood is sucked n through the end-face suction opening 37 of the pump housing 32 and conveyed backward within the pump housing 32 in the axial direction. Through outlet openings 38 in the pump housing 32 the blood flows out of the pump section 12 and further along the motor housing 20. This ensures that the heat produced in the drive is carried off. It is also possible to operate the pump section with the reverse conveying direction, with blood being sucked in along the motor housing 20 and exiting from the opening 37.

The motor shaft 25 is mounted in radial bearings 27 and 31 at the proximal end of the motor housing, on the one hand, and at the distal end of the motor housing, on the other hand. The radial bearings are in this exemplary embodiment respectively configured as simple sliding bearings. Furthermore, the motor shaft 25 is also mounted axially in the motor housing 20. The axial bearing 40 is likewise configured as a sliding bearing. The axial sliding bearing 40 will be explained more precisely hereinafter with reference to FIG. 3. It serves for taking up axial forces of the motor shaft 25 which act in the distal direction when the impeller 34 conveys from distal to proximal. Should the blood pump be used for conveying blood also or only in the reverse direction, a corresponding axial sliding bearing 40 is (also/only) to be provided at the proximal end of the motor housing 20 in a corresponding manner.

The blood pump according to FIG. 2 can alternatively be employed without purge fluid for short-term use over a few hours. In this case the sliding bearings are lubricated once, and the distal sliding bearing 31 is moreover furnished with a radial lip seal in order to prevent the entry of blood. A purge-fluid line can then advantageously be omitted altogether.

FIG. 3 shows the detail HI from FIG. 2 in greater detail. There can be seen in particular the radial sliding bearing 31 and the axial sliding bearing 40. The bearing gap of the radial sliding bearing 31 is formed, on the one hand, by the circumferential surface of the motor shaft 25, which is DLC-coated, and, on the other hand, by the surface of the through bore in the distal end wall 30 of the motor housing 20, which is manufactured as a ceramic part, for example of zirconium oxide.

The bearing gap of the axial sliding bearing 40 is formed, on the one hand, by the axially interior surface 41 of the end wall 30 and a surface 42 opposing it. This opposing surface 42 is part of a ceramic disk 44 which is seated on the motor shaft 25 distally of the rotor 26 and rotates with the rotor 26. A channel 43 in the bearing-gap surface 41 of the end wall 30 ensures that purge fluid can flow through between the bearing-gap surfaces 41 and 42 of the axial sliding bearing 40 to the radial sliding bearing 31 and exit from the motor housing 20 distally. The purge fluid is chosen to have a viscosity of at least 1.2 mPa·s at 37° C. A suitable fluid has turned out to be 20% glucose solution, for example. The axial sliding bearing 40 represented in FIG. 3 is a normal sliding bearing. Hydrostatic sliding-bearing variants will be described hereinafter with reference to FIGS. 6A/B, 7 and 8. Unlike the representation, the axial gap of the axial sliding bearing 40 is very small, being a few μm.

Instead of the axial sliding bearing 40 and radial sliding bearing 31, there can also be realized a combined radial-axial sliding bearing 46 having a concave bearing shell in which a convex bearing surface runs. Such a variant is represented in FIG. 4 by a spherical sliding bearing 46. The bearing-gap surface 41 is of spherically concave design, and the opposing bearing-gap surface 42 is of corresponding spherically convex design. The channel 43 again lies in the stationary bearing-gap surface 41 of the end wall 30. Alternatively, the stationary bearing-gap surface 41 of the end wall 30 can be of convex configuration and the opposing bearing-gap surface 42 of concave configuration. The surfaces 42, 43 can also be conical instead of spherical. Preferably, a corresponding radial-axial sliding bearing is provided on both sides of the motor housing 20 in order not to permit any radial offset upon axial travel of the shaft 25. The advantage of a combined axial-radial sliding bearing lies in the higher loading capacity. However, a disadvantage is the greater frictional diameter.

FIG. 5 shows the radial bearing 27 at the distal end of the motor housing 20. Here, too, the motor shaft 25 is furnished with a DLC coating and runs in a bearing bush which forms an integral part of the proximal end wall 22, again made of ceramic, of the motor housing 20. Thus far, the radial sliding bearing 27 corresponds to the radial sliding bearing 31.

Distributed over the circumference of the end wall 22 there are provided three axially extending slots 50 spaced at 120°, of which only one is to be seen in FIG. 2. Through these slots 50, thin lead wires 51 lead to the windings of the stator 24. The lead wires 51 are soldered on the proximal side of the end wall 20, the soldering point 52 having been previously made conductive with a local copper coating. At the same soldering point 52 the end of the power supply line 23 is also soldered. The connection of the wires of the stator windings with the power supply lines can be effected with all conventional joining methods (soldering, welding, clamping, laser welding, gap welding, contact bonding, etc.). Subsequently the end wall 22 including the lead wires 51 and the soldering points 52 is encased in a plastic material, with the motor windings of the stator also being encased at the same time. This can be effected by vacuum casting by way of example.

The previously described blood pump does without radial ball bearings for mounting the motor shaft 25, which are hard to mount and possess a minimum size of 3 min. This makes it possible to manufacture pumps having even smaller outer diameters of for example only 3 mm. Moreover, the service life of this blood pump is considerably increased compared with those having radial ball bearings on account of lower wear. Run times >30 days can thus be realized with low wear. The latter is extremely significant, since the mounting and the true running of the impeller are vital for low blood damage.

FIG. 6A shows in plan view the surface 41 of the distal end wall 30 of the motor housing 20 according to an alternative exemplary embodiment. FIG. 6B shows a development of the surface 41 from FIG. 6A. The surface 41 itself is stationary. The direction indicated by the arrow indicates in which direction the opposing surface 42 of the sliding bearing 40 moves. This then also corresponds to the direction in which the lubricating film moves within the bearing gap relative to the stationary surface 41. Accordingly, the surface 41 possesses ramps disposed one behind the other which form converging gaps together with the opposing moved surface 42, which is even. This causes a hydrodynamic pressure to build up in the lubricating film, which ensures that the surfaces forming the bearing gap remain at a distance.

A configuration of the rotating surface with the ramp-like structures according to FIGS. 6A and 69 is advantageous for the efficiency of the axial sliding bearing, but leads to an elevated radial conveying effect in the bearing gap which is opposed to the conveying direction of the purge fluid. FIG. 7 represents the simplest form of a ramp-like realization of the convergent gap in the form of a wobble disk. Here, the disk 44 is simply installed on a slant or minimally beveled. The slant typically amounts to 1 to 5 μm.

FIG. 8 shows another variant for a hydrodynamically acting surface of the axial sliding bearing 40. This involves a so-called spiral groove bearing, which is preferably formed on the moving surface of the bearing gap, i.e. accordingly on the surface 42 of the ceramic disk 44. In this case, several grooves 45 are spirally disposed in the surface 42. The grooves 45 are indicated only schematically in FIG. 8. When the ceramic disk 44 rotates in the direction indicated by the arrow in FIG. 8, the lubricating film is conveyed radially inward along the grooves 45 and builds up a pressure there which in turn ensures that the surfaces forming the bearing gap are kept at a distance apart.

The invention claimed is:

1. An intravascular blood pump, comprising:
   a drive section having a motor housing with a proximal end and a distal end and further having an electric motor disposed in the motor housing, the electric motor possessing a motor shaft which protrudes out of the distal end of the motor housing, the motor shaft being radially mounted in the motor housing by a first radial bearing located at the proximal end of the motor housing and a second radial bearing located at the distal end of the motor housing, wherein at least one of the first and second radial bearings of the motor shaft is configured as a radial sliding bearing, and wherein the motor shaft is axially mounted within the motor housing by at least one of an axial sliding bearing and a radial-axial sliding bearing;
   a catheter connected to the proximal end of the motor housing, the catheter comprising lines for power supply to the electric motor;
   a pump section having a tubular pump housing fastened to the distal end of the motor housing and further comprising an impeller disposed on a distal end of the motor shaft, the impeller configured to rotate within the tubular pump housing; and a purge-fluid line, wherein the motor shaft is made of ceramic, wherein the at least one radial sliding bearing comprises an inner surface forming a bearing gap with a ceramic surface of the motor shaft, wherein the motor shaft is radially mounted in the motor housing by exactly two bearings which are maximally removed from each other and positioned at the proximal end and the distal end of the motor housing, wherein the radial bearing located at the distal end of the motor housing is configured as the radial sliding bearing, and wherein the purge-fluid line is positioned such that purge fluid fed through the purge-fluid line flows through the bearing gap of the radial sliding bearing.

2. The intravascular blood pump of claim 1, wherein the axial sliding bearing or the radial-axial sliding bearing comprises a disk disposed on the motor shaft and supported against a circumferential shoulder of the motor housing.

3. The intravascular blood pump of claim 1, wherein one or more surfaces forming the bearing gap of the axial sliding bearing or the radial-axial sliding bearing has a channel which penetrates the bearing gap of the axial sliding bearing or the radial-axial sliding bearing from radially outward to radially inward.

4. The intravascular blood pump of claim 3, wherein the bearing gap of the axial sliding bearing or the radial-axial sliding bearing is configured as a converging gap in some regions in a circumferential direction.

5. The intravascular blood pump of claim 1, wherein the ceramic is zirconium oxide.

6. The intravascular blood pump of claim 1, wherein the first radial bearing situated at the proximal end of the motor housing has an outer ring, and lead wires of the electric motor extend through the outer ring or within a radially outwardly located slot of the outer ring.

7. The intravascular blood pump of claim 6, wherein the lead wires of the electric motor and the lines extending along the catheter are connected electroconductively with soldering on a surface located proximally of the first radial bearing situated at the proximal end of the motor housing.

8. The intravascular blood pump of claim 7, wherein at least one of the motor housing and the soldering is at least partly encased in a cast plastic housing.

9. The intravascular blood pump of claim 1, wherein a total distal end of the motor housing, including a surface of at least one of the axial sliding bearing and the radial-axial sliding bearing, is manufactured as a one-piece ceramic part.

10. The intravascular blood pump of claim 1, wherein the electric motor comprises a rotor, and wherein at least one of the axial sliding bearing and the radial-axial sliding bearing is formed by an axially interior surface of an end wall of the motor housing and an opposing surface in a form of a ceramic disc seated on the motor shaft distally of the rotor and rotating with the rotor.

11. The intravascular blood pump of claim 1, wherein the inner surface forming the bearing gap of the radial sliding bearing is a ceramic surface formed by an end wall of the motor housing.

12. The intravascular blood pump of claim 11, wherein the ceramic surface formed by the end wall of the motor housing is formed by a through bore in a distal end wall of the motor housing.

13. The intravascular blood pump of claim 11, wherein the ceramic surface formed by the end wall of the motor housing is formed by a bearing bush which forms an integral part of a proximal end wall of the motor housing.

14. A system comprising the intravascular blood pump of claim 1 and a purge-fluid source for supplying the purge-fluid line with a purge fluid whose viscosity at 37° C. lies >1.2 mPa·s.

15. A method for supporting blood circulation while employing the intravascular blood pump of claim 1, wherein the purge fluid fed to the purge-fluid line has a viscosity lying >1.2 mPa·s at 37° C.

16. The method of claim 15, wherein the purge fluid is a >20% glucose solution.

17. An intravascular blood pump, comprising:

a drive section having a motor housing with a proximal end and a distal end and further having an electric motor disposed in the motor housing, the electric motor possessing a motor shaft which protrudes out of the distal end of the motor housing, the motor shaft being radially mounted in the motor housing by a first radial bearing located at the proximal end of the motor housing and a second radial bearing located at the distal end of the motor housing, wherein at least one of the first and second radial bearings of the motor shaft is configured as a radial sliding bearing, and wherein the motor shaft is axially mounted within the motor housing by at least one of an axial sliding bearing and a radial-axial sliding bearing;

a catheter connected to the proximal end of the motor housing, the catheter comprising lines for power supply to the electric motor; and a pump section having a tubular pump housing fastened to the distal end of the motor housing and further comprising an impeller disposed on a distal end of the motor shaft, the impeller configured to rotate within the tubular pump housing, wherein the motor shaft is made of ceramic, wherein the at least one radial sliding bearing comprises an inner surface forming a bearing gap with a ceramic surface of the motor shaft, wherein the motor shaft is radially mounted in the motor housing by exactly two bearings which are maximally removed from each other and positioned at the proximal end and the distal end of the motor housing, wherein one or more surfaces forming a bearing gap of the axial sliding bearing or the radial-axial sliding bearing has a channel which penetrates the bearing gap of the axial sliding bearing or the radial-axial sliding bearing from radially outward to radially inward, and wherein the one or more surfaces forming the bearing gap of the axial sliding bearing or the radial-axial sliding bearing are configured to be moved relative to other surfaces.

18. The intravascular blood pump of claim 17, wherein the one or more surfaces forming the bearing gap of the axial sliding bearing or the radial-axial sliding bearing that has moved relative to other surfaces is even.

19. The intravascular blood pump of claim 17, wherein the one or more surfaces forming the bearing gap of the axial sliding bearing that has moved relative to other surfaces comprises one or more spirally disposed grooves.

* * * * *